US011124466B2

(12) United States Patent
Tanimu et al.

(10) Patent No.: US 11,124,466 B2
(45) Date of Patent: Sep. 21, 2021

(54) PRODUCTION OF LIGHT ALKENES FROM ALKANE

(71) Applicant: King Fahd University of Petroleum and Minerals, Dhahran (SA)

(72) Inventors: Gazali Tanimu, Dhahran (SA); Ziyauddin S. Qureshi, Dhahran (SA); Sachio Asaoka, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/564,762

(22) Filed: Sep. 9, 2019

(65) Prior Publication Data

US 2021/0070674 A1 Mar. 11, 2021

(51) Int. Cl.
| | |
|---|---|
| *C07C 5/48* | (2006.01) |
| *B01J 23/84* | (2006.01) |
| *C07C 11/08* | (2006.01) |
| *B01J 23/843* | (2006.01) |
| *B01J 35/02* | (2006.01) |
| *B01J 37/08* | (2006.01) |

(52) U.S. Cl.
CPC ............ *C07C 5/48* (2013.01); *B01J 23/8437* (2013.01); *B01J 35/023* (2013.01); *B01J 37/08* (2013.01); *C07C 11/08* (2013.01)

(58) Field of Classification Search
CPC .. C07C 5/48; C07C 5/42; B01J 23/843; B01J 37/08; B01J 35/02
See application file for complete search history.

(56) References Cited

U.S. PATENT DOCUMENTS

| | | | |
|---|---|---|---|
| 3,745,194 A | 7/1973 | Bertus et al. | |
| 5,639,929 A * | 6/1997 | Bharadwaj | ............... C07C 5/48 585/654 |
| 8,088,962 B2 * | 1/2012 | Klanner | ............... C07C 5/3337 585/325 |
| 10,125,061 B2 | 11/2018 | Aljundi | |

FOREIGN PATENT DOCUMENTS

| | | |
|---|---|---|
| CA | 2 428 200 | 5/2002 |
| CN | 1308075 C | 4/2007 |
| CN | 01734987 B | 11/2012 |

OTHER PUBLICATIONS

Tanimu et al. (Effect of support in Ni—Bi—O/support catalyst on oxidative dehydrogenation of n-butane to butadiene, Jun. 16, 2017, Molecular Catalysis, vol. 438, pp. 245-255). (Year: 2017).*
Tanimu, et al. ; Effect of support in Ni—Bi—O/support catalyst on oxidative dehydrogenation of n-butane to butadiene ; Molecular Catalysis, vol. 438 ; pp. 245-255 ; Sep. 2017 ; Abstract Only ; 2 Pages.
Maia, et al. ; Isobutane and n-butane cracking on Ni-ZSM-5 catalyst: Effect on light olefin formation ; Applied Catalysis A: General 403 ; pp. 58-64 ; Jun. 17, 2011 ; 7 Pages.

* cited by examiner

*Primary Examiner* — Youngsul Jeong
(74) *Attorney, Agent, or Firm* — Oblon, McClelland, Maier & Neustadt, L.L.P.

(57) ABSTRACT

A method of oxidative dehydrogenating of butane stream comprises contacting the same with a bimetallic catalyst in the presence of oxygen, wherein the bimetallic catalyst containing nickel and bismuth or oxides thereof supported on solid support such as zirconium oxide, low aluminum MFI zeolite, and mesoporous silica foam. Various embodiments of the method of oxidative dehydrogenating the butane-containing hydrocarbon stream and the bimetallic catalyst are also provided.

19 Claims, No Drawings

PRODUCTION OF LIGHT ALKENES FROM ALKANE

BACKGROUND OF THE INVENTION

Field of the Invention

The present invention relates to a method of producing alkene from alkane by oxidative dehydrogenation.

Description of the Related Art

The "background" description provided herein is for the purpose of generally presenting the context of the disclosure. All references cited herein are incorporated by reference. Work of the presently named inventors, to the extent it is described in this background section, as well as aspects of the description which may not otherwise qualify as prior art at the time of filing, are neither expressly or impliedly admitted as prior art against the present disclosure.

Increased demand for light olefins which are widely used in the polymer and petrochemical industries has provided motivation for identifying new production methods that are more efficient and economical than conventional methods, in particular, methods utilizing alkanes as starting materials. Olefins such as ethylene and propylene are considered as the backbone of the petrochemical industry. Light alkanes having 2-6 carbon atoms are available and are relatively less expensive compared to alkenes having the same number of carbon atoms. That provides an economic motivation to develop efficient methods for converting alkanes to alkenes. Such methods have the added advantage of being considered more environmentally friendly than other methods currently in use, and hence, alkanes have been widely used as a raw material in the production of petrochemicals [Nieto, J. L. "The selective oxidative activation of light alkanes. From supported vanadia to multicomponent bulk V-containing catalysts" *Top. Catal.*, vol. 41, pp. 3-15, 2006; and Téllez et al. "Oxidative Dehydrogenation of Butane over VMgO Catalysts," *J. Catal.*, vol. 195, pp. 113-124, 2000]. Among all alkenes, ethylene and propylene are the most used petrochemicals for the production of polymers such as polyethylene, polypropylene, polystyrene, polyacrylonitrile, and polyethylene oxide. About 60% of propylene produced worldwide is used in the production of thermoplastic polypropylene. The global production capacity of ethylene and propylene is forecasted to reach 385 million tons in 2030 increasing from 240 million tons in 2016 [Fagg, L. "Long-term Sustainability in Commodity Petrochemicals: An outlook for olefins and aromatics", *Asia Petrochemical Industry Conference (APIC)*, Amghizar, I., Vandewalle, L., Van Geem, K., Marin, G. New Trends in Olefin Production, Engineering, vol 3, pp. 171-178, 2017].

Butadiene is used mainly as a monomer in the manufacture of polymers such as synthetic rubbers including styrene butadiene rubber (SBR), polybutadiene rubber (PBR), and nitrile rubber. Such polymers are durable and/or elastic [Vasil'ev and Galich "Catalysts for the oxidative dehydrogenation of butenes and butane to butadiene" *Chem. Technol. Fuels Oils*, vol. 33, pp. 185-192, 1997; and Veldurthi et al. "Promotional effects of Cu on Pt/Al$_2$O$_3$ and Pd/Al$_2$O$_3$ catalysts during n-butane dehydrogenation," *Catal. Today*, vol. 185, pp. 88-93, 2012].

Commercial methods for alkene production include steam cracking which a gaseous one-phase homogeneous reaction is occurring at temperatures greater than 800° C. Steam cracking involves the decomposition of hydrocarbon feedstocks using steam to produce different products such as alkenes, alkanes and molecular hydrogen [Al-Ghamdi, S. A. "Oxygen-Free Propane Oxidative Dehydrogenation Over Vanadium Oxide Catalysts: Reactivity and Kinetic Modelling" December, 2013, Ph. D. Thesis, University of Western Ontario, Canada—incorporated herein by reference in its entirety. Fluid catalytic cracking (FCC) is used for upgrading streams from refineries. It produces higher value products such as gasoline from vacuum gas oil and de-asphalted oil. Ethylene is mainly produced by naphtha steam cracking in addition to other feedstocks such as ethane and liquefied petroleum gas (LPG). Propylene is obtained as byproduct of FCC and naphtha steam cracking. By varying the operating conditions and additives, the yield of propylene can be enhanced. Also, propylene can be produced from propane dehydrogenation. These processes produce high purity olefins in an acceptable yield at relatively high energy cost due to the endothermic nature of the reactions involved. Also, they produce coke which deactivates the catalyst used in the processes. In addition, selectivity is difficult to control at such temperatures [Rodriguez et al. "Dehydrogenation of n-butane over Pd—Ga/Al$_2$O$_3$ catalysts" *Appl. Catal. A Gen.*, vol. 373, pp. 66-70, 2010; and Mamedov and Corberan, "Oxidative dehydrogenation of lower alkanes on vanadium oxide-based catalysts. The present state of the art and outlooks" *Appl. Catal. A, Gen.*, vol. 127, pp. 1-40, 1995, each incorporated herein by reference in their entirety]. The current methodologies for producing alkenes are believed to have reached their full potential and cannot accommodate the ever-increasing demands of the petrochemical industry.

Catalytic oxidative conversion of alkanes has been utilized as an alternative process for the production of alkenes including ethylene, propylene, and butene isomers as well as butadiene. The process has relatively low operating cost and reduced environmental impact. The catalytic oxidative conversion of alkanes is an exothermic process producing alkenes at lower temperature. Catalytic oxidative catalysts are auto-activated by oxygen provided in the feed stream and do not require an additional re-oxidation step. Thus, the presence of oxygen within the hydrocarbon feed stream not only reduces coking but also extends the catalyst life time [Malaika et al. "Chemically Modified Activated Carbons as Catalysts of Oxidative Dehydrogenation of n-Butane,"*Acta Phys. Pol. A*, vol. 118, pp. 459-464, 2010, incorporated herein by reference in its entirety]. In addition, the formation of water as a byproduct provides additional advantage by continuously removing the hydrogen gas produced in the reaction mixture, and thereby avoids the thermodynamic limitations associated with conventional methods [Heracleous et al. "Oxidative dehydrogenation of ethane and propane over vanadia and molybdena supported catalysts" *J. Mol. Catal. A Chem.*, vol. 232, pp. 29-39, 2005, incorporated herein by reference in its entirety].

Jermy and co-workers investigated the catalytic oxidative conversion of alkanes targeted mainly at producing butadiene as a second step dehydrogenation product [Jermy et al "Oxidative dehydrogenation of n-butane to butadiene over Bi—Ni—O/γ-alumina catalyst" *J. Mol. Catal. A Chem.*, vol. 400, pp. 121-131, 2015; Jermy et al. "Influence of calcination on performance of Bi—Ni—O/gamma-alumina catalyst for n-butane oxidative dehydrogenation to butadiene," *Catal. Sci. Technol.*, vol. 5, pp. 4622-4635, 2015; and Tanimu et al. "Composition effect of metal species in (Ni, Fe, Co)—Bi—O/gamma-alumina catalyst on oxidative dehydrogenation of n-butane to butadiene," *J. Ind. Eng. Chem.*, vol. 45, pp. 111-120, 2017, each incorporated herein by reference in their entirety]. Several metal oxide catalysts including monometallic, bimetallic and ternary metallic combinations were evaluated. The role of the support in dispersing the metal oxides and the influence of calcination temperature on the catalytic activities were also evaluated. The results showed that both ethylene and propylene were coproduced at lower yields, which was highly dependent on the nature of active oxygen species and the acid-base character of the catalyst.

CN101734987B discloses a method for preparing ethylene and propylene from C4 hydrocarbons. The method comprises introducing a C4 hydrocarbon into a reactor comprising a dehydrogenation catalyst to produce an alkene followed by introducing the resulting alkene to a second reactor containing a cracking catalyst to obtain ethylene and propylene. The dehydrogenation catalysts are platinum, palladium, nickel, cobalt, and chromium supported on silicon dioxide, diatomite, or pumice. The cracking catalysts are acidic natural or synthetic molecular sieve, silicon oxide, and alumina. The method disclosed in CN101734987B is a two-step method carried out in sequence.

CN1308075C discloses a catalyst system for converting alkanes to alkenes and to their corresponding oxygenated products. The catalyst system comprises at least one element such as gold, silver, iridium, nickel, palladium, platinum, rhodium, ruthenium and at least one modifier metal oxide such as bismuth, indium, magnesium, phosphorous, antimony, and zirconium.

U.S. Pat. No. 3,745,194A discloses a dehydrogenation catalyst consisting of tin associated with at least one metal such as bismuth, cobalt, or nickel to convert C4 to C10 alkane to alkene in the presence of oxygen. The ratio of tin to bismuth, cobalt, or nickel is in the range of 3:1 to 1:3. The catalyst may be supported on silica, alumina, or silica-alumina. The main product of the method disclosed in U.S. Pat. No. 3,745,194A patent is 1,3-butadiene obtained through oxidative dehydrogenation alkanes.

U.S. Ser. No. 10/125,061B2 (incorporated herein by reference in its entirety) discloses a butane dehydrogenation method comprising passing a stream of butane on nickel oxide and bismuth oxide catalyst supported on titanium carbide in the presence of oxygen at a temperature in the range of 400° C. to 500° C. The U.S. Ser. No. 10/125,061B2 method is mainly concerned about the production of 1-butene, cis- and trans-2-butene as well as butadiene.

CA2428200A1 discloses an electrochemical method for the conversion of alkane to at least one corresponding alkene. The method is carried out in an electrochemical cell comprising an anode chamber containing the alkane, a cathode chamber comprising oxygen, and comprises passing a proton through a medium from the cathode chamber to the anode chamber. The disclosed method in the CA2428200A1 is directed to a method for producing propylene, butanes, and styrene.

Tanimu et al. [Mol. Cat. (2017) 438, 245-255] examine the effect of the catalyst support on the activity and selectivity of oxidative dehydrogenation of n-butane to butadiene catalyzed by $NiO/Bi_2O_3$. The order of selectivity for butadiene is a catalyst supported on $Al_2O_3>SiO_2>ZrO_2>>$None.

Maia et al. [Appl. Catal. A: General 403 (2011) 58-64] disclose Ni-ZSM-5 as a catalyst to obtain light olefin from isobutene and n-butane. Nickel (0.4-6 wt %) was introduced into H-ZSM-5 zeolite by dry impregnation and ionic exchange methods. Also, Maia et al. disclose a method of converting the alkanes to propylene and ethylene at a temperature of 500° C. and comprises heating the catalyst under nitrogen and introducing isobutane or n-butane with nitrogen gas as a carrier.

In view of the foregoing discussions, one of the objectives of the present invention is to provide a process for the catalytic oxidative conversion of a hydrocarbon stream comprising butane to ethylene and propylene using a supported bimetallic catalyst at relatively low pressure and temperature in comparison to those of conventional processes to provide improved yield and product selectivity.

SUMMARY OF THE INVENTION

According to a first aspect, the present disclosure relates to a method of dehydrogenating a butane-containing hydrocarbon stream comprises contacting a mixture of the butane-containing hydrocarbon stream and oxygen with a bimetallic catalyst supported on a solid support selected from the group consisting of zirconium oxide, low aluminum MFI zeolite, and mesoporous silica foam to form a product stream comprising one or more oxygenated products, ethylene and propylene, wherein the bimetallic catalyst consists of nickel oxide and bismuth oxide.

In one embodiment, the method further comprises separating the ethylene and the propylene product from the oxygenated products.

In one embodiment, the hydrocarbon stream comprises butane, isobutene, rafinate, or combination thereof.

In one embodiment, the butane is n-butane.

In one embodiment, the raffinate is one or more of raffinate-I, raffinate-II, rafinate-III, rafinate-IV, or a combination thereof.

In one embodiment, the bimetallic catalyst is prepared by impregnating un-calcined solid support with nickel oxide and bismuth oxide.

In one embodiment, the un-calcined solid support zirconium oxide, zirconium hydroxide or combination thereof.

In one embodiment, the mixture comprises oxygen and butane in an oxygen/butane molar ratio in the range of 1 to 6.

In one embodiment, the solid support is modified with Fe, Co, Ga, Mo and/or W.

In one embodiment, the catalyst comprises a weight percent of nickel in the bimetallic catalyst is within a range of 15 wt % to 25 wt %, relative to the total weight of the bimetallic catalyst.

In one embodiment, the catalyst comprises a weight percent of bismuth in the bimetallic catalyst is within a range of 25 wt % to 35 wt %, relative to the total weight of the bimetallic catalyst.

In one embodiment, the bimetallic catalyst supported on solid support is subjected to calcination at 250-400° C. for at least 0.5 h and 560-640° C. for at least 1 h prior to the contacting.

In one embodiment, the butane-containing hydrocarbon stream is contacted with the bimetallic catalyst supported on the solid support at a temperature of 400 to 600° C.

In one embodiment, the bimetallic catalyst has an average particle size in the range of 0.1 to 2 mm.

In one embodiment, the method further comprising treating the bimetallic catalyst supported on the solid support with an inert gas having a temperature in a range of 300 to 600° C. prior to the contacting.

In one embodiment, the butane-containing hydrocarbon stream is at a pressure in the range of 1-10 bars during contacting.

In one embodiment, wherein the product stream comprises the ethylene and propylene molar in a molar ratio of (moles of ethylene and moles of propylene):(all other compounds in the product stream) at least 0.6.

In one embodiment, a conversion of butane to ethylene and propylene is in a range of 5 to 30 mol %, and wherein a combined yield of ethylene and propene is in the range of 3 to 25 mol % based on the conversion of butane.

In one embodiment, the method further comprises mixing the mixture of butane-containing hydrocarbon stream and oxygen with an inert gas prior to the contacting, wherein a volume fraction of the butane-containing hydrocarbon stream is within a range of 0.01 to 0.1.

In one embodiment, the butane-containing hydrocarbon stream is contacted with the bimetallic catalyst at a temperature of 450 to 550° C., and wherein a molar ratio of oxygen to butane is in a range of 1:1 to 6:1.

In one embodiment, a method of dehydrogenating a butane-containing hydrocarbon stream, comprising:

contacting a mixture of the butane-containing hydrocarbon stream and oxygen at a pressure in the range of 1-10 bar with a bimetallic catalyst supported on a solid support selected from the group consisting of zirconium oxide, low aluminum MFI zeolite, and mesoporous silica foam to form a product stream comprising ethylene and propylene, wherein the butane-containing hydrocarbon stream is contacted with the bimetallic catalyst at a temperature of 450 to 550° C.

In one embodiment, a molar ratio of oxygen to butane is in a range of 1:1 to 6:1.

DETAILED DESCRIPTION

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising" "include," "includes," and "including" are interchangeable and not intended to be limiting.

Unless otherwise specified, "a" or "an" means "one or more".

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items.

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

A first aspect of the invention is directed to a method of oxidative and dehydrogenation of a butane-containing hydrocarbon stream to produce ethylene and propylene.

As used herein the term "dehydrogenation" refers to a chemical reaction that involves removal of hydrogen from an organic molecule. In addition, "oxidative dehydrogenation" refers to a chemical reaction that involves the removal of hydrogen from an organic molecule in the presence of an oxidant such as molecular oxygen. Accordingly, in aspects of the present disclosure a butane-containing hydrocarbon stream is contacted with a bimetallic catalyst in the presence of an oxidant such as oxygen gas, wherein at least a portion of butane present in the butane-containing hydrocarbon stream is oxidatively dehydrogenated accompanied by the loss of at least one carbon and one hydrogen molecule. As a result, a product stream that includes ethylene and propylene in addition to one more compounds other than ethylene and propylene such as but not limited to butene, cis- and trans-isobutene, butadiene, propane, carbon dioxide, and carbon monoxide may form.

In one embodiment, the butane-containing hydrocarbon stream includes butane and one or more hydrocarbon compounds selected from the group consisting of alkanes, alkenes, dienes, aromatics, and mixtures thereof. The term "alkane" as used herein refers to saturated straight-chain, saturated branched, or saturated cyclic hydrocarbons having a carbon number in the range of 1 to 12, preferably 2 to 6, such as methane, ethane, propane, pentane, hexane, heptane, octane, nonane, decane, and the like. The terms "alkene" and "olefin" are used herein interchangeably having the same meaning and refer to a hydrocarbon compound comprising at least one double bond such as ethylene, propylene, 1-butene, cis- or trans-2-butene, pentene, cyclopentene, hexane, cyclohexene, butadiene, and the like. Also, the terms "diolefin" and "diene" as used herein interchangeably to refer to hydrocarbon compounds having two conjugated or unconjugated double bonds that may be present in the butane-containing hydrocarbon stream or the resulting product stream. These include, but are not limited to propadiene, butadiene, isoprene, pentadiene, cyclopentadiene, hexadiene, and the like. Additionally, exemplary oxygenated compounds that may be present in the butane-containing hydrocarbon stream and/or the resulting product stream include, but are not limited to water, tert-butanol, methyl tert-butyl ether, methanol, ethanol, acetic acid, acetaldehyde, acetone, and the like. In one embodiment, a volume fraction of butane in the butane-containing hydrocarbon stream is at least 0.4, at least 0.5, at least 0.6, at least 0.7, at least 0.8, at least 0.9, preferably at least 0.92, preferably at least 0.95, preferably at least 0.98, preferably at least 0.99. In some embodiments, the butane-containing hydrocarbon stream is in a liquid state, and a mass fraction of butane in the butane-containing hydrocarbon stream is at least 0.5, at least 0.6, preferably at least 0.7, preferably at least 0.8, preferably at least 0.9. Preferably, a volume fraction of non-butane compounds present in the butane-containing hydrocarbon stream is no more than 0.1, preferably no more than 0.08, preferably no more than 0.05, preferably no more than 0.02. Exemplary non-butane compounds that may be present in the butane-containing hydrocarbon stream include, but are not limited to, methane, ethane, propane, pentane, hexane, ethylene, propylene, pentene, hexane, propadiene, butadiene, pentadiene, tert-butanol, methyl tert-butyl ether, methanol, ethanol, acetic acid, acetaldehyde, water, and the like. The butane-containing hydrocarbon stream may be an effluent from a debutanizer, a fluid catalytic cracker, a steam cracker, a separation column, or a combination thereof. In an alternative embodiment, at least a portion of the alkane present in the butane-containing hydrocarbon stream is oxidatively dehydrogenated in the presence of the bimetallic catalyst and the oxidant, via an oxidative dehydrogenation reaction to produce alkenes and oxygenated products In one embodiment, the butane-containing hydrocarbon stream is in a gaseous state when contacted with the bimetallic catalyst. In another embodiment, the butane-containing hydrocarbon stream is in a liquid/gaseous state, wherein liquid reactants present in the butane-containing hydrocarbon stream may be vaporized by methods and devices known in the art prior to be contacted with the bimetallic catalyst. Alternatively, the butane-containing hydrocarbon stream may be in a liquid state.

In some embodiments, the butane-containing hydrocarbon stream may contain any gaseous or low boiling fraction distillate obtained from petroleum refinery processes; such as but not limited to: normal butane, isobutene, light petroleum gas, butane-butene mixtures, and raffinate. Raffinates are light petroleum gas or liquefied petroleum gas mixtures (LPG or LP gas) that are flammable mixtures of hydrocarbon gases, mostly a mixture of propane and butane. They are often formed as byproduct fractions of a naphtha cracking process. Raffinate-I (C4R1) refers to C4 residual compounds obtained after separating 1,3-butadiene from a C4 raffinate stream and which, mainly contain isobutylene 40~50 wt % and cis- or trans-2-butene 30~35 wt %. Raffinate-II (C4R2) refers to C4 residual obtained after separation of 1,3-butadiene and isobutylene from C4 a raffinate stream and which mainly consists of cis- or trans-2-butene 50~60 wt %, 1-butene 10~15 wt %, and n-butane ~20 wt %. Raffinate-III (C4R3) refers to C4 residual obtained after separation of 1,3-butadiene, isobutylene, and 1-butene from a C4 raffinate stream which mainly contains cis- or trans-2-butene, n-butane, and unseparated 1-butene. Raffinate-4 (C4R4) refers to C4 residual obtained after separation of 1,3-butadiene, isobutylene, 1-butene, and cis- or trans-2-butene from a C4 raffinate stream which mainly contains n-butane.

The oxidant is preferably a gaseous oxidant, but may also include a liquid oxidant or a solid-state oxidant. The gaseous oxidant is preferably molecular oxygen, and may be present as an oxygen stream or as an oxygen-containing stream. The oxygen-containing stream may be air, or an oxygen stream that has been diluted with one or more inert gases such as nitrogen, argon, helium, and the like. Other gaseous oxidants, such as, but not limited to $N_2O$, $NO$, or $NO_2$ may also be used for oxidatively dehydrogenating the butane-containing hydrocarbon stream. In embodiments wherein a solid-state oxidant is used, the oxidant may be periodically regenerated. In a preferred embodiment, the oxidant is an oxygen-containing stream which is mixed with the butane-containing hydrocarbon stream such that a molar ratio of oxygen to butane is in the range of 1:1 to 1:8, preferably 1:1 to 1:7, preferably 1:1 to 1:6, preferably 1:1 to 1:5, and preferably 1:1 to 1:4.

The bimetallic catalyst used in the invention comprises nickel and bismuth supported on any solid support such as but not limited to zirconium oxide, low-aluminum zeolite, mesoporous silica foam. In a preferred embodiment, nickel is used in the bimetallic catalyst, Nickel, as the term is used herein, refers to elemental nickel, although in some embodiments, nickel as used in the bimetallic catalyst is present in the form of a nickel oxide, a nickel salt, or mixtures thereof. Additionally, in a preferred embodiment, bismuth used in the bimetallic catalyst refers to elemental bismuth, although in some embodiments the bismuth may be present in the form of a bismuth oxide, a bismuth salt, or mixtures thereof. Furthermore, in some embodiments, the bimetallic catalyst includes elemental nickel and one or more of a nickel oxide and a nickel salt; and elemental bismuth and one or more of a bismuth oxide and a bismuth salt. In an alternative embodiment, nickel and bismuth are present in the bimetallic catalyst as a form of a bimetallic alloy of NiBi and/or $Ni_xBi_y$, wherein x and y are integers in the range of 1 to 10, preferably 1 to 5, preferably 1 to 3.

In one embodiment, a weight percent of nickel (present as elemental nickel, a nickel oxide, and/or a nickel salt) in the bimetallic catalyst is within the range of 15 wt % to 25 wt %, preferably 16 wt % to 24 wt %, preferably 17 wt % to 23 wt %, preferably 18 wt % to 22 wt %, preferably 19 wt % to 21 wt %, preferably about 20 wt %, relative to the total weight of the bimetallic catalyst. In another embodiment, a weight percent of bismuth (present as elemental bismuth, a bismuth oxide, and/or a bismuth salt) in the bimetallic catalyst is within the range of 25 wt % to 35 wt %, preferably 26 wt % to 34 wt %, preferably 27 wt % to 33 wt %, preferably 28 wt % to 32 wt %, preferably 29 wt % to 31 wt %, preferably about 30 wt %, relative to the total weight of the bimetallic catalyst. In an alternative embodiment, a weight ratio of bismuth to nickel in the bimetallic catalyst is in the range of 1:1 to 3:1, preferably 1.1:1 to 2:1, preferably 1.2:1 to 1.8:1, preferably 1.3:1 to 1.5:1, preferably about 1.4:1. In some embodiments, nickel and bismuth as used in the bimetallic catalyst are nanoparticles with an average particle size in the range of 5 to 50 nm, preferably 8 to 30 nm, preferably 10 to 15 nm that are deposited on a surface of a support such as but not limited to zirconium oxide or low-aluminum zeolite or mesoporous silica foam.

The term "bimetallic catalyst" as used herein refers to a catalyst that includes nickel and bismuth as major metallic elements (i.e. having a weight percent of at least 15 wt %, preferably at least 18 wt %, preferably at least 20 wt %, relative to the total weight of the bimetallic catalyst), and thus provide a major contribution to catalyze the oxidative dehydrogenation reactions. However, a catalyst support may also be a catalytically active in the oxidative dehydrogenation reaction.

The term "bimetallic" is not meant to be limiting to two metallic elements, and thus more than two metallic elements may also be present in a composition of the bimetallic catalyst. However, metallic elements other than nickel and bismuth may also be present as minor elements, i.e., having a weight percent of up to 10 wt %, preferably up to 8 wt %, preferably up to 5 wt %, and down to 0.01 wt %, preferably down to 0.05 wt %, preferably down to 0.1 wt %, relative to the total weight of the bimetallic catalyst. Accordingly, in one embodiment, the bimetallic catalyst includes a third element selected from titanium (Ti), tantalum (Ta), niobium (Nb), iron (Fe), cobalt (Co), gallium (Ga), molybdenum (Mo), hafnium (Hf), tungsten (W), yttrium (Y), zinc (Zn), zirconium (Zr), aluminum (Al), and/or a compound containing one or more of such element(s) for example oxides or salts of such elements, or mixtures thereof. Preferably, a weight percent of the third element may be less than 10 wt %, preferably less than 8 wt %, preferably less than 5 wt %, and down to 0.01 wt %, preferably down to 0.05 wt %, preferably down to 0.1 wt % relative to the total weight of the bimetallic catalyst. Alternatively, the third element may be an alkali metal, an alkaline earth metal, an oxide thereof, a salt thereof, or a mixture of such elements or compounds. For example, in one embodiment, the third element is selected from the group consisting of Ca, K, Mg, Sr, Ba, Li, and Na, most preferably Ca, K and Mg, and in either case, oxides thereof and salts thereof, or mixtures of such elements or compounds. In one embodiment, the third element is a basic metal oxide to adjust an acidity of the bimetallic catalyst. An oxide of an element is an oxide thereof where the respective element is in an oxidation state other than the fully-reduced state, and includes oxides having an oxidation states corresponding to known stable valence numbers, as well as to oxides in partially reduced oxidation states. In addition, a salt of an element can be any stable salt thereof, including, for example, nitrates, carbonates, and acetates. Preferably, other metals that are not listed above may not be present in the bimetallic catalyst.

In a preferred embodiment, the support may be any suitable porous solid support with a pore size ranging from 2 nm to 100 nm, preferably 5 nm to 80 nm, preferably 10 nm to 60 nm, preferably 15 nm to 50 nm, preferably 20 nm to 40 nm. Additionally, the catalyst support may have a surface area ranging from 0.5 $m^2$/g to 300 $m^2$/g, preferably 5 $m^2$/g to 250 $m^2$/g, preferably 15 $m^2$/g to 200 $m^2$/g, preferably 20 $m^2$/g to 150 $m^2$/g, preferably 25 $m^2$/g to 100 $m^2$/g. In view of this embodiment, nickel, bismuth, and/or the third element (if present) may be present on a surface of the catalyst support, or inside the pores. Examples of suitable supports include but not limited to silica, alumina, zeolite, activated carbon, titania, zirconia, and magnesia. In some embodiments, a second catalyst support may be used in the composition of the bimetallic catalyst to modify porosity and/or a surface area of the primary support of the bimetallic catalyst. In view of that, a weight percent of the second catalyst support relative to the weight of the primary support is no more than 20%, preferably no more than 15%, preferably no more than 10%. In the embodiments, where the second catalyst support contains a catalytically active element (e.g., $Al_2O_3$ that contains aluminum), the second catalyst support may catalyze the oxidative dehydrogenation reactions. In some other embodiments, the second catalyst support is inert, and does not participate in the oxidative dehydrogenation reactions.

In some embodiments, the bimetallic catalyst is supported on one or more supports such as zirconia, low aluminum zeolite, preferably low aluminum zeolite MFI, or mesoporous silica, preferably mesoporous silica foam.

As used herein the terms "zirconia" and "zirconium oxide" have the same meaning referring to zirconium dioxide. The porous zirconia may be obtained from a commercial source or prepared by well-known method in the art such as described by any of U.S. Pat. Nos. 4,203,772; 5,128,291; 5,275,759; 7,642,210; 7,927699; and 9,956,543—each of which incorporated herein by reference in its entirety. The porous zirconia catalyst support preferably has a BET surface area of 20-500 $m^2$/g, for example a BET surface area of at least 20, at least 50, at least 100, at least 150 and at least 350 $m^2$/g. In preferred embodiments, the zirconia has surface area in the range of 150 to 250 $m^2$/g, or about 200 to 220 $m^2$/g. The zirconia-based porous support has a pore diameter of at least 20 nm, preferably at least 30 nm, at least 40 nm, at least 50 nm, at least 60 nm, at least 70 nm, at least 80 nm, at least 90, at least 100 nm or more, and a total pore volume of at least 0.1 mL/g, preferably at least 0.2 mL/g, at least 0.4 mL/g, 0.5 mL/g, 0.6 mL/g, at least 0.7 mL/g, at least 0.8 mL/g, at least 0.9 mL/g, at least 1.0 mL/g or more.

Zeolites are the aluminosilicate members of a family of microporous solids known as "molecular sieves", and mainly contain Si, Al, O, and other metals including but not limited to Ti, Sn, and Zn. The term molecular sieve refers to a particular property of zeolite, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels, which are conventionally defined by the ring size of the aperture. For example, the term "8-ring" refers to a closed loop that is built from eight tetrahedrally coordinated silicon and/or aluminum atoms and 8 oxygen atoms. The rings are not always perfectly symmetrical for variety of reasons that include strain induced by the bonding between units needed to produce the overall structure, or coordination of some of the oxygen atoms of the rings to cations within the structure. Therefore, the pores in many zeolites are not cylindrical. Zeolites may be natural or synthetic material and their pore structure can accommodate a wide variety of cations, such as, but not limited to $Na^+$, $K^+$, $Ca^{2+}$, and $Mg^{2+}$. The positive ions are loosely held in the zeolite matrix and can readily be exchanged for others in a contact solution. Some of the more common mineral zeolites are analcime, chabazite, clinoptilolite, heulandite, natrolite, phillipsite, and stilbite. An example of the mineral formula of a zeolite is: $Na_2Al_2Si_3O_{10} \cdot 2H_2O$, the formula for natrolite. The cation exchanged zeolites have different acidity and therefore, have catalytic activity. In some preferred embodiment, the zeolite support of the bimetallic catalyst is synthetic.

In some preferred embodiments, the bimetallic catalyst is supported on a zeolite having an MFI structure such as ZSM-5 and the like. Further, the zeolite may contain an oxide other than silica and alumina in the crystal structure. The zeolite support used to support the bimetallic catalyst preferably has low aluminum content. As used herein the term "low aluminum content" refers to a zeolite having an atomic ratio of silicon to aluminum (Si/Al) of at least 50, preferably 100, preferably 150, preferably 200, preferably 250, preferably 300, preferably 350. Further, the zeolite catalyst used in the present invention preferably contains an alkaline earth metal (AEM) such as calcium, strontium and the like, and it has an atomic ratio of the AEM to aluminum (AEM/Al) in the catalyst of 0.5 or more, preferably 0.75 to 15 and more preferably 2 to 8. The zeolite catalyst containing such an AEM may be prepared by well-known methods in the art. Here, the atomic ratio, Si/Al and AEM/Al may be determined by a conventional analytical method, for example, such as atomic absorption spectrometry, inductively coupled plasma emission spectrometry and the like, or either by the stoichiometric ratio of the silicon-containing compound to the aluminum-containing compound used for the synthesis of the zeolite or the stoichiometric ratio of a compound containing an AEM to the aluminum-containing compound. In one embodiment, the bimetallic catalyst is supported on law aluminum zeolite MFI.

Another preferred support for the bimetallic catalyst is mesoporous silica such as, but not limited to mesoporous nanoparticles MCM-41 and SBA-15. Mesoporous silica nanoparticles are synthesized by reacting tetraethyl orthosilicate (TEOS) with a template such as but not limited to micelles or polymers, preferably rod shaped micelles. The result is a collection of nano-sized spheres or rods that are filled with a regular arrangement of pores. The template can then be removed by washing with aqueous solution adjusted to a proper pH or by calcination at a temperature in the range of 300-600° C. Also, mesoporous particles may be synthesized by a sol-gel method, or a spray drying method. A more effective precursor for the synthesis of the mesoporous silica is (3-mercaptopropyl)trimethoxysilane (MPTMS). The use MPTMS as precursor is reported to reduce aggregation and ensures more uniform spheres.

In some preferred embodiments, the bimetallic catalyst is supported mesoporous foam. As used in herein, "mesoporous silica foam" means an amorphous mesoporous silica foam, i.e., a silica support with a non-ordered structure and a narrow pore size distribution. The non-ordered structure may be random and thus, different than the other mesoporous silica which have hexagonal or cubic structures. Specifically, the mesoporous silica foam has a narrow pore size distribution of at least 3 nm to about 40 nm and a total pore volume of at least 0.500 $cm^3/g$, preferably 0.600 $cm^3/g$, preferably, 0.700 $cm^3/g$, 0.800 $cm^3/g$, preferably 0.900 $cm^3/g$, preferably 1.0 $cm^3/g$, preferably 1.50 $cm^3/g$, preferably 2.0 $cm^3/g$, preferably 2.50 $cm^3/g$. Without being bound by theory, the present pore size distribution and pore volume are sized to achieve better catalytic activity and reduced blocking of pores by metal oxides, whereas smaller pore volume and pore size support are susceptible to pore blocking and thereby reduced catalytic activity of the bimetallic catalyst. Reducing the blocking of the pores leads to higher dispersion of Ni—Bi catalytic species on the amorphous mesoporous silica foam. Higher Ni—Bi dispersion leads to higher catalytic activity and thus, higher ethylene and propylene yield.

In one or more embodiments, the pore size distribution of the mesoporous silica foam impregnated with bimetallic catalyst may range from at least 3 nm to about 40 nm, or from about 3 nm to about 20 nm, or from about 4 nm to about 10 nm, or from about 4 nm to about 8 nm, or from about 4 nm to about 6 nm. Moreover, mesoporous silica foam impregnated with bimetallic catalyst may have a total acidity in the range of 0.125 mmol/g to 0.500 mmol/g. In further embodiments, the amorphous mesoporous silica foam impregnated with the bimetallic catalyst may have a total acidity from about 0.125 mmol/g to about 0.250 mmol/g, or from about 0.125 mmol/g to about 0.150 mmol/g. While various surface areas are contemplated, the bimetallic catalyst may, in one or more embodiments, have a surface area of at least about 400 $m^2/g$, or in the range of 400 $m^2/g$ to about 800 $m^2/g$, preferably 400 $m^2/g$ to about 500 $m^2/g$, preferably 400 $m^2/g$ to about 450 $m^2/g$, preferably 425 $m^2/g$ to about 450 $m^2/g$.

The bimetallic catalyst may be prepared by any well-known method in the art from metal precursors which are generally metal salts. Examples of suitable metal salts include but are not limited to metal alkoxides, chlorides, bromides, iodides, nitrates, and carboxylates. Typically, the metal precursors of nickel and bismuth are added to an aqueous medium which may contain a water miscible solvent such as, but not limited to methanol, ethanol, propanol, isopropanol, and ethylene glycol to form a reaction mixture. The reaction mixture may be acidic at a pH in the range of 3-6, neutral pH about 7, or basic at pH in the range of 8-13, and may be stirred and/or heated at a temperature in the range of 45-95° C., preferably 50-85° C., preferably 55-75° C. for at least 0.5 h, preferably 1.0, preferably 1.5 h, preferably 2 h, preferably 3 h, preferably 4 h, preferably 5 h, preferably 6 h. A calcined or un-calcined support may be added to the reaction mixture before heating or after heating to form a suspension. The amount of solid support in the catalyst is at least 50 wt. %, preferably at least 55 wt. %, preferably at least 60 wt. %, preferably, preferably 70% of the total weight of the catalyst. The suspension is generally cooled to ambient temperature and stirred for at least 5 h, preferably 7 h, preferably 8 h, preferably 9 h, preferably 12 h to impregnate the support with the metals or their oxides or salt.

In a preferred embodiment, the bimetallic catalyst is prepared by impregnating an un-calcined or calcined solid support such as, but not limited to zirconium oxide, aluminum MFI zeolite or mesoporous silica foam with the catalyst material.

In one embodiment, the bimetallic catalyst may be mixed with binders and/or diluents, which are known to those of skilled in the art to reduce a concentration and an acidity of the bimetallic catalyst. Diluents may be added to the catalyst in the range of 0 to 30 vol %, preferably 5 to 25 vol %, preferably 10 to 20 vol %, relative to the total volume of a catalyst bed that houses the catalyst and the diluents. The diluents may improve the heat removal or heat transfer of the bimetallic catalyst to help avoid hot spots or to modify hot spots. Additionally, binders may provide mechanical strength to the catalyst and may be added to the bimetallic catalyst in the range of 0 to 30 vol %, preferably 5 to 25 vol %, preferably 10 to 20 vol %, relative to the total volume of the catalyst/binder. Preferable binders include silica sol, silica, alumina, diatomaceous earth, hydrated zirconia, silica aluminas, alumina phosphates, naturally occurring materials, cements and combinations thereof. Preferable diluents include, for example, quartz chips, sands, clay and/or cement.

Preferably, the bimetallic catalyst may be pressed to form in disc-shape pellets having a diameter in the range of 0.1-2 min, preferably 0.2-1.5 mm, more preferably about 1 mm. The bimetallic catalyst may also be pressed to form a powder, granules, pellets, extrudates, or a shaped catalyst. Accordingly, the bimetallic catalyst may have a cylindrical (solid or hollow cylindrical), a spherical, a rectilinear, a star-shape, a ring-shape, a conical, a pyramidal, a rectangular, or a cubical geometry with an average particle size in the range of 0.1-2 mm, preferably 0.2-1.5 mm, more preferably about 1 mm. Shaping of the bimetallic catalyst may be carried out by compaction (for example tableting or extrusion) of a solid catalyst mixture with or without a prior kneading step, if necessary with addition of conventional auxiliaries (e.g., graphite or stearic acid or its salts as lubricants). In some embodiments, the solid catalyst mixture may be shaped either before or after calcining the catalyst, for example, by grinding the solid catalyst mixture before or after calcination.

In one embodiment, the bimetallic catalyst is housed in a catalyst bed of a reactor, and the butane-containing hydrocarbon stream and the oxidant are delivered to the reactor either together as a mixed gas through a common feed line, or separately but simultaneously via different feed lines. The reactor may preferably be a fixed-bed reactor, although other reactors such as a batch reactor or a fluidized bed reactor may also be employed.

In one embodiment, the butane-containing hydrocarbon stream is mixed with an inert gas to form a gaseous mixture prior to contacting with the bimetallic catalyst. A volume fraction of the butane-containing hydrocarbon stream in the gaseous mixture is preferably within the range of 0.01 to 0.1, more preferably 0.02 to 0.08, preferably 0.03 to 0.05, preferably about 0.04. Preferably, the inert gas may be at least one gas selected from nitrogen, argon, and carbon dioxide.

In one embodiment, the butane-containing hydrocarbon stream, the oxidant, and the bimetallic catalyst may be contacted by passing a mixture of the butane-containing hydrocarbon stream and the oxidant through a fixed-bed reactor packed with the bimetallic catalyst, or by passing said mixture over an exposed surface of the bimetallic catalyst. The contact time (or residence tune) may vary, however, preferably the contact time may range from about 0.1 seconds to about 10 seconds, preferably from about 0.5 seconds to about 8 seconds, preferably from about 1 seconds to about 5 seconds. In another embodiment, the butane-containing hydrocarbon stream and the oxidant are in a gaseous state, wherein a gas space velocity may range from about 100/hr to about 10,000/hr, preferably from about 300/hr to about 6,000/hr, and more preferably from about 300/hr to about 2,000/hr. In one embodiment, the inert gas is used to adjust the gas space velocity. In another embodiment, the butane-containing hydrocarbon stream and the oxidant are contacted with the bimetallic catalyst at a temperature that ranges from about 300° C. to about 600° C., more preferably from about 320° C. to about 550° C., even more preferably from about 350° C. to about 520° C., still more preferably from about 375° C. to about 500° C., and yet more preferably from about 390° C. to about 475° C., and most preferably from about 400° C. to about 470° C. In another embodiment, the butane-containing hydrocarbon stream and the oxidant are contacted with the bimetallic catalyst at a pressure that ranges from atmospheric pressure (i.e. 1 atm) to about 20 bars, preferably from about 1.5 bars to about 10 bars, preferably from about 2 bars to about 8 bars, preferably from about 2.5 bars to about 5 bars.

The product stream includes ethylene and propylene, one or more non-ethylene compounds, one or more non-propylene compounds, and water. The non-ethylene and non-propylene compounds which may be present in the product stream include one or more of 1-butene, cis-2-butene, trans-2-butene, 1,3-butadiene, and isobutylene produced from n-butane or isobutane. In one embodiment, one or more other products may be formed such as methane, ethane and butadiene. The product stream has a combined molar ratio of the ethylene and propylene to other compounds of at least 0.5, preferably 0.6, preferably 0.7, preferably 0.8, preferably 0.9. In one embodiment, halide-substituted alkanes (preferably having a carbon number of 2 to 5) are oxidatively dehydrogenated using the bimetallic catalyst to form vinyl halides. For example, ethyl chloride may be oxidatively dehydrogenated using the bimetallic catalyst and methods described herein to form vinyl chloride. In addition, the product stream may further include unreacted alkanes, an unreacted oxidant, as well as side-products (e.g., $CO_2$). Ethylene and propylene may be separated from the product stream by well-known method in the art including but not limited to cryogenic separation, by pressure-swing adsorption (e.g., on zeolites), by selective absorption, and the like.

In an alternative embodiment, the product stream may be used, without further separation or with partial separation (e.g., with a removal of $CO_2$ and/or $H_2O$) as a feed stream to a downstream reactor, where the alkene product can be reacted further.

In some embodiments, the ethylene produced via oxidative dehydrogenation of n-butane using the bimetallic catalyst may be further reacted to form polyethylene, styrene, ethanol, acetaldehyde, acetic acid, vinyl chloride, ethylene oxide, ethylene glycol, ethylene carbonate, ethyl acetate, and vinyl acetate. For example, ethylene may be polymerized to form polyethylene according to methods known in the art using a catalyst having activity for polymerizing ethylene to polyethylene. Exemplary polymerization approaches include free-radical polymerization and polymerization over Ziegler-Natta (i.e., metal alkyl) catalysts. Ethylene may also be reacted with benzene in the presence of acid catalysts such as aluminum chloride or zeolites to form ethylbenzene, which may further be catalytically dehydrogenated (using the bimetallic catalyst of the invention or known dehydrogenation catalysts) to form styrene. Styrene may also be formed directly from a reaction of ethylene and benzene. Moreover, ethylene may be hydrated to form ethanol according to methods known in the art using a catalyst comprising an element or compound having activity for hydrating ethylene to ethanol (e.g. catalysts that include oxides of B, Ga, Al, Sn, Sb or Zn, or mixtures of such oxides), along with a water stream that is preferably co-fed to a reaction zone during the hydration reaction. Acetaldehyde may also be formed from ethylene according to methods known in the art either directly or through an ethanol intermediate. Accordingly, ethylene can be oxidized to acetaldehyde using a catalyst comprising an element or a compound having activity for oxidizing ethylene to acetaldehyde (e.g. catalysts that include oxides of Pd, Cu, V or Co, or mixtures of such oxides). Alternatively, ethylene may be hydrated to form ethanol and ethanol is then oxidized to form acetaldehyde in the presence of a catalyst having activity for oxidizing ethanol to acetaldehyde (e.g. catalysts that include metals and/or metal oxides of Cu, Co, Ag, Re, Ru, Pt, Bi, Ce, Sb, In, Pd, Rh, Ir, V, Cr or Mn, or mixtures of such oxides). Furthermore, ethylene may be oxidized to form acetic acid according to methods known in the art using a catalyst comprising an element or compound having activity for oxidizing ethylene to acetic acid (e.g. catalysts that include a noble metal or an oxide thereof, preferably Pd or Pt or oxides thereof), along with a water stream that is preferably co-fed to a reaction zone during the ethylene oxidation reaction. Besides, ethylene may be chlorinated or oxychlorinated to form vinyl chloride according to methods known in the art. In a chlorination reaction, chlorine or other chlorinating agent may be preferably co-fed to the reaction zone, and ethylene is chlorinated in the presence of a catalyst having activity for chlorinating ethylene to vinyl chloride (e.g. catalysts that include a metal halide or a metal oxyhalide, and preferably a halide or an oxyhalide of Cu, Fe, or Cr), or alternatively in the absence of a catalyst. In an oxychlorination reaction, a gaseous oxidant and HCl or other chlorinating agent may preferably be co-fed to the reaction zone, and ethylene is oxychlorinated in the presence of a catalyst having activity for oxychlorinating ethylene to vinyl chloride (e.g. catalysts that include a metal halide or a metal oxyhalide, preferably a halide or an oxyhalide of Cu, Fe, or Cr). Yet, ethylene may be oxidized to form ethylene oxide according to methods known in the art using a catalyst comprising an element or compound having activity for oxidizing ethylene to ethylene oxide (e.g. catalysts that include Ag, a halide thereof, an oxide thereof or a salt thereof). Ethylene glycol may be produced by oxidizing ethylene to ethylene oxide as described above, and hydrating ethylene oxide to form ethylene glycol. Ethylene carbonate may be produced from ethylene by reacting ethylene with carbon dioxide or carbon monoxide to form ethylene carbonate, or alternatively by forming ethylene glycol as described above and then reacting the ethylene glycol with phosgene. Ethyl acetate may be formed from acetic acid, prepared as described above, according to methods known in the art. Vinyl acetate may also be prepared by vapor-phase reaction of ethylene, acetic acid and oxygen over a Pd catalyst.

In some embodiments, propylene produced via oxidative dehydrogenation of propane using the bimetallic catalyst may be further reacted to form polypropylene, acrolein, acrylic acid, acetone, propylene oxide, and propylene carbonate. Propylene may be optionally purified, and then further reacted according to one or more of the following schemes. For example, in one embodiment, propylene can be polymerized to form polypropylene according to methods known in the art using a catalyst having activity for polymerizing propylene to polypropylene (e.g. aluminum alkyl catalysts). In another embodiment, propylene is oxidized to form acrolein according to methods known in the art using a catalyst comprising an element or compound having activity for oxidizing propylene to acrolein (e.g. catalysts that include an oxide of Bi, Mo, Te or W, or mixtures of such oxides). In another embodiment, propylene is oxidized to form acrylic acid according to methods known in the art using a catalyst comprising an element or compound having activity for oxidizing propylene to acrylic acid (e.g. catalysts that include an oxide of Mo, V or W, or mixtures of such oxides). Acetone may be produced from propylene by oxidation of propylene. Propylene may also be oxidized to form propylene oxide according to methods known in the art using a catalyst comprising an element or compound having activity for oxidizing propylene to propylene oxide (e.g. catalysts that include TiSi oxide or PdTiSi oxide). In one embodiment, propylene carbonate is formed by preparing propylene oxide as described above, and by reacting the propylene oxide with carbon dioxide. Propylene can also be directly converted to propylene carbonate in a single-step process.

In other embodiments, non-ethylene and non-propylene compounds/olefins such as n-butene or isobutene are formed in the product stream which may be purified, and then further reacted to form useful products. For example, isobutene may be oxidized to form methacrylic acid according to methods known in the art using a catalyst comprising an element or compound having activity for oxidizing isobutene to methacrylic acid (e.g. catalysts that include polyoxometallate (POM), preferably PVMo- or PVW-containing POM). Butanol may be prepared by hydrating n-butene to form butanol. Alternatively, n-butene may be oxidatively dehydrogenated to form butadiene according to methods known in the art using a catalyst comprising an element or compound having activity for oxidatively dehydrogenating n-butene to butadiene (e.g. catalysts that include elements or compounds selected from the group consisting of Ni, Ti, Ta, Nb, Hf, W, Y, Zn, Zr, Al, oxides thereof, and salts thereof, or mixtures of such elements or compounds). Butanediol may also be prepared by forming butadiene, as described above and then hydrating butadiene to form butanediol. Moreover, n-butene may be oxidatively dehydrogenated to form butadiene, and butadiene can be oxidized to form methylethylketone (MEK) according to the methods known in the art using a catalyst comprising an element or compound having activity for oxidation of butadiene to MEK (e.g. catalysts that include Bi/Mo, Mo/V/W, VPO or a polyoxometallate). Alternatively, n-butene may be oxidatively dehydrogenated to form butadiene (as described above), and butadiene can be oxidized to form methylvinylketone (MVK) according to the methods known in the art using a catalyst comprising an element or compound having activity for oxidation of butadiene to MVK (e.g. catalysts that include Bi/Mo, Mo/V/W, VPO or a polyoxometallate).

In one embodiment, furan is prepared by oxidizing n-butene. Crotonaldehyde can also be prepared by forming butadiene, as described above and oxidizing butadiene to form crotonaldehyde.

In a preferred embodiment, the butane-containing hydrocarbon stream, the oxidant, the bimetallic catalyst loading, and reaction conditions are controlled to achieve a reaction performance that is suitable for industrial applications. Accordingly, in one embodiment, the butane-containing hydrocarbon stream, the oxidant, the bimetallic catalyst loading, and reaction conditions are controlled such that butane is dehydrogenated to ethylene and propylene with a butane conversion of at least about 5% by mole, preferably at least about 10% by mole, preferably at least about 15% by mole, preferably at least about 20% by mole, preferably at least about 25% by mole, but no more than 30% by mole, and a selectivity of at least about 70% by mole, preferably at least about 75% by mole, preferably at least about 80% by mole, preferably at least about 85% by mole, preferably at least about 90% by mole. In another embodiment, the butane-containing hydrocarbon stream, the oxidant, the bimetallic catalyst loading, and reaction conditions are controlled such that butane is dehydrogenated to ethylene and propylene with a butane conversion in the range of 5% to 30% by mole, preferably 8% to 25% by mole, preferably 10% to 22% by mole, preferably 11% to 20% by mole, preferably 15% to 20% by mole, and a selectivity of ethylene and propylene compounds in the range of 80% to 95% by mole, preferably 82% to 92% by mole, preferably 85% to 90% by mole. In some embodiments, a selectivity of ethylene is in the range of 3% to 60% by mole, preferably 5% to 55% by mole, preferably 20% to 55% by mole, preferably 30% to 45% by mole. In other embodiments, a selectivity of propylene is in the range of 1% to 30% by mole, preferably 3% to 25% by mole, preferably 5% to 20% by mole, preferably 7% to 15% by mole.

As used herein, the term "butane conversion" refers to the percentage of the amount (by mole) of butane provided to a reaction zone of a reactor via the butane-containing hydrocarbon stream, which is converted to carbon products.

As used herein, the term "selectivity" refers to the percentage of the amount (by mole) of butane that is converted to ethylene and/or propylene. In addition, the selectivity of oxygenation and cracking reactions refers to the amount (by mole) of butane that is converted via oxygenation and cracking reactions, and the selectivity of partial oxidation reactions refers to the amount (by mole) of butane that is converted via partial oxidation reactions. Alternatively, the "selectivity" is defined as a molar ratio of the combined molar amount of ethylene and propylene to the other compounds present in the product stream. In one embodiment, the selectivity is substantially independent of the butane conversion.

In view of the above definitions of the butane conversion and the selectivity, a yield of ethylene and propylene based on the butane conversion may be defined as a multiplication of the butane conversion and the selectivity. Accordingly, in one embodiment, the yield of the ethylene and propylene is in the range of 2% to 20%, preferably 3% to 15%, preferably 4% to 12%, based on the butane conversion, which is in the range of 5% to 30%, preferably 8% to 25%, preferably 10% to 22%, preferably 11% to 20%, preferably 15% to 20%.

The bimetallic catalyst of the present invention offers significant performance advantages as compared to currently used catalysts for oxidative dehydrogenation of butane such as VMo, $MgO/ZrO_2$, or $VMgO/MgO/ZrO_2$ catalysts. For example, the catalysts of the invention may result a butane conversion of about 15% to 20% and a selectivity of about 60% to 90%, compared to a butane conversion of about 5% and a selectivity of about 90% for conventional catalysts.

In one embodiment, the bimetallic catalyst of the present disclosure is stable with respect to a dehydrogenation activity and performance characteristics. Stability of the bimetallic catalyst can be demonstrated by a lifetime testing, wherein the butane-containing hydrocarbon stream and the oxidant are co-fed to a reaction zone of a reactor containing the bimetallic catalyst, while maintaining the reaction zone (and the bimetallic catalyst) at a temperature that ranges from about 200° C. to about 600° C., preferably from about 300° C. to about 550° C., preferably from about 350° C. to about 520° C., preferably from about 375° C. to about 500° C., preferably from about 390° C. to about 475° C., preferably from about 400° C. to about 470° C. The butane-containing hydrocarbon stream is contacted continuously with the bimetallic catalyst in the presence of the oxidant to dehydrogenate butane (and other alkanes present in the butane-containing hydrocarbon stream) and to form ethylene and propylene as well as other corresponding alkenes. The ethylene, propylene, other alkenes, unreacted alkanes and unreacted oxidants are contentiously exhausted or otherwise removed from the reaction zone. In a preferred embodiment, the steps of contacting the butane-containing hydrocarbon stream and the oxidant with the catalyst, dehydrogenating the alkanes, and exhausting the alkenes and unreacted reactants are carried out in a continuous cumulative period of not less than about 200 hours, preferably not less than about 400 hours, more preferably not less than about 600 hours, even more preferably not less than about 1000 hours, and most preferably not less than about 2000 hours. Accordingly, the bimetallic catalyst may preferably be stable for at least about 5000 hours, and more preferably at least about 8000 hours.

In one embodiment, the bimetallic catalyst is treated with an inert gas before contacting the butane-containing hydrocarbon stream and the oxidant with the catalyst. The inert gas is preferably at least one selected from nitrogen, argon, helium and carbon dioxide. Treating the bimetallic catalyst is performed to bring a temperature of the catalyst to a preferable temperature, in which oxidative dehydrogenation is carried out. In view of that, the inert gas may have a temperature from about 200° C. to about 600° C., preferably from about 300° C. to about 550° C., preferably from about 350° C. to about 520° C., preferably from about 375° C. to about 500° C., preferably from about 390° C. to about 475° C., preferably from about 400° C. to about 470° C. In another embodiment, at least a portion of the product stream is recycled to be contacted with the bimetallic catalyst. Recycling at least a portion of the product stream may result in an overall improvement in the butane conversion and the selectivity. For example, in one embodiment, recycling at least a portion of the product stream may increase the butane conversion by at least 5%, preferably at least 10%, but no more than 30%. In a preferred embodiment, unreacted alkanes of the product stream are first separated from ethylene, propylene, and other alkenes, and then the unreacted alkanes are recycled to be contacted with the bimetallic catalyst.

Although the present invention is described and exemplified primarily in connection with oxidative dehydrogenation of butane, dehydrogenation of other alkanes using the bimetallic catalyst and the method disclosed herein may also be contemplated, and is within the scope of the invention. For example, cyclohexane may be oxidatively dehydrogenated over the bimetallic catalyst of the invention to form benzene. Moreover, the bimetallic catalyst of the invention may be used for dehydrogenating alkenes to one or more dehydrogenation products, e.g. dienes or alkynes. Similarly, butenes may be dehydrogenated to form ethylene, butylene, butadiene, and isoamylene may be dehydrogenated to form isoprene.

Another aspect of the invention relates to a method of producing the bimetallic catalyst. The method involves dissolving a nickel precursor and a bismuth precursor in water, preferably deionized water, to form a Ni—Bi solution. In a preferred embodiment, the nickel precursor is a metal salt of nickel and a counter ion selected from nitrate, acetate, oxalate, and halide. For example, in one embodiment, the nickel precursor is nickel nitrate, preferably nickel nitrate hexahydrate. In another preferred embodiment, the bismuth precursor is a metal salt of bismuth and a counter ion selected from nitrate, acetate, oxalate, and halide. For example, in one embodiment, the bismuth precursor is bismuth nitrate, preferably bismuth nitrate pentahydrate.

The nickel and the bismuth precursors may be in the form of a sol-gel that include nickel or bismuth along with one or more counter ions selected from nitrate, acetate, oxalate, a halide, and an alkoxide. Additionally, the nickel and the bismuth precursors may be dissolved in a solvent such as water, aqueous organic solvent, or organic solvent (e.g. methanol, toluene, tetrahydrofuran, ethylene glycol, etc.). When a halide is used as a counter ion, a resulting bimetallic catalyst is preferably rinsed with water to remove halide. For example, in one embodiment, the nickel precursor is nickel nitrate along with potassium bromide, wherein a resulting bimetallic catalyst is preferably rinsed with water to remove potassium bromide. In one embodiment, the Ni—Bi solution further includes a third precursor to provide the third element to the bimetallic catalyst. The third precursor may preferably be a salt of Ti, Nb, Ta, and Zr, for example, titanium oxalate, niobium oxalate, tantalum oxalate, or zirconium oxalate.

In one embodiment, a concentration of nickel in the Ni—Bi solution is in the range of 5 to 7 g/L, preferably 5.2 to 6.8 g/L, preferably 5.5 to 6.7 g/L, preferably 5.8 to 6.5 g/L, preferably about 6.2 g/L. In another embodiment, a concentration of bismuth in the Ni—Bi solution is in the range of 7 to 9 g/L, preferably 7.5 to 8.9 g/L, preferably 8 to 8.8 g/L, preferably 8.5 to 8.7 g/L, preferably about 8.65 g/L. To achieve the Ni—Bi solution having the aforementioned concentration of nickel and bismuth, in one embodiment, 0.75 to 1.25 g, preferably 0.95 to 1.05 g, preferably about 1 g of the nickel precursor is dissolved in 140 to 180 ml, preferably 150 to 170 ml, preferably 160 ml of water, preferably distilled water. Then, 1.3 to 1.5 g, preferably 1.35 to 1.45 g, preferably about 1.39 g of the bismuth precursor is mixed with the resulting solution to form the Ni—Bi solution. Preferably, the Ni—Bi solution may be stirred at an elevated temperature of 30 to 70° C., preferably 40 to 65° C., preferably 50 to 60° C., preferably about 55° C. to dissolve the nickel and the bismuth precursor in water. In the embodiments where a third precursor is present to provide the third element to the composition of the bimetallic catalyst, a concentration of the third element in the Ni—Bi solution is no more than 2 g/L, preferably no more than 1 g/L, preferably no more than 0.5 g/L.

The method further involves mixing and a catalyst support with the Ni—Bi solution to form a suspension. The suspension is maintained at a temperature in the range of 20 to 60° C., preferably 24 to 50° C., preferably 26 to 40° C., preferably about 25° C., for at least 6 hours, preferably at least 8 hours, preferably at least 12 hours, preferably at least 24 hours, during which nickel and bismuth are deposited on a surface a support particles. Any suitable porous catalyst support known in the art may be used in the preparation of the catalyst of the invention such as but not limited to porous carbon, silica, metal oxides such as, but not limited zinc oxide, vanadium oxide, magnesium oxide, magnesium oxide, and the like, zeolite, and the like. In preferred embodiment, the support is at least one of at least zirconium oxide, low aluminum MFI zeolite, and mesoporous silica foam. The ability of the zirconium oxide, low aluminum zeolite, or mesoporous silica foam to improve the dispersion of the active metal oxide system coupled with the availability of lattice oxygen species selective for oxygenate and cracking products have a major positive impact on the oxidative dehydrogenation reaction. The support may be calcined or un-calcined when added to the solution comprising Ni—Bi precursor. In a preferred embodiment, the support is un-calcined as it produces a catalyst that is more uniformly dispersed on the surface of the support. In a preferred embodiment, a weight ratio of bismuth to nickel in the suspension is in the range of 1:1 to 2:1, preferably in the range of 1.2:1 to 1.5:1, preferably about 1.4:1. In a preferred embodiment, a ratio of the amount of the support particles to a volume of the Ni—Bi solution depends on a pore volume of the support particles, and may range from about 50 to about 150, preferably from about 70 to about 90 times the pore volume of the support particles. For example, in one embodiment, 1.5 to 2.5 g, preferably 2 g of support particles are used for 140 to 180 ml, preferably 150 to 170 ml, preferably 160 ml of the Ni—Bi solution, wherein the support particles have a specific pore volume in the range of 0.5 to 3 ml/g, preferably about 1.5 ml/g. In one embodiment, a pH of the suspension is maintained at about 2 to about 6.5, preferably about 3 to about 6, preferably about 4 to about 6.

The method further involves drying the suspension. Accordingly, the suspension may be dried preferably at a reduced pressure (i.e. a sub atmospheric pressure of less than 0.9 atm, preferably less than 0.5 atm), and at a temperature ranging from about 80° C. to about 150° C., preferably from about 100° C. to about 140° C., preferably about 120° C., for a period of time ranging from about 1 hour to about 5 hours, preferably 2 to 4 hours, preferably about 3 hours.

Alternatively, the suspension may be dried by other methods known in the art such as lyophilization, precipitation, and/or evaporation. Lyophilization refers to freezing the suspension (e.g., under liquid nitrogen), and then placing a frozen suspension in a vacuum so that water (i.e. ice) sublimes, leaving behind a solid pre-calcination composition that includes the bimetallic catalyst. Precipitation refers to a method of separating a solute from a solvent via adding one or more chemical reagents that can selectively precipitate the solute (i.e. the bimetallic catalyst) from the solvent (i.e. water). The chemical reagents may provide ions that shift ionic equilibrium to favor formation of insoluble metal salts, or may bind with bismuth, nickel, or other elements present on the catalyst support to form uncharged and water insoluble coordination compounds. The chemical reagents may also oxidize or reduce bismuth, nickel, or other elements present on the catalyst support to form ionic species that produce water insoluble salts. Regardless of a precipitation mechanism used, precipitated compounds (i.e. the bimetallic catalyst) may be separated from the remaining suspension by first centrifuging the suspension and then decanting a supernatant. Residual water present in the solid pre-calcination composition may be removed by evaporation via heating and/or under vacuum. Preferably, the solid pre-calcination composition may be achieved in a form of a powder that includes the bimetallic catalyst.

In some embodiments, the method further involves pressing the powder to form pellets of the bimetallic catalyst with an average pellet particle size in the range of 0.1 to 2 mm, preferably 0.2-1.5 mm, more preferably 0.4 to 1 mm, even more preferably 0.5 to 0.9 mm. The pellets may further be crushed to form bimetallic catalyst granules, and said granules may further be sieved to form finer granules with an average particle size in the range of 0.1 to 1 mm, preferably 0.2-0.8 mm. Having the bimetallic catalyst in the form of pellets or granules may provide a consistent bulk density of the catalyst and/or a consistent pressure drop across a catalyst bed of a reactor that houses the bimetallic catalyst.

In a preferred embodiment, the bimetallic catalyst granules is calcined via a two-step calcining process, wherein the bimetallic catalyst granules is first calcined at a temperature in the range of 300 to 400° C., preferably 320 to 380° C., preferably 340 to 360° C., preferably about 350° C., for no more than 2 hours, preferably no more than 1 hour. Next, the already calcined catalyst is calcined for a second time at a temperature in the range of 500 to 900° C., preferably 550 to 700° C., preferably 570 to 620° C., preferably about 590° C., for no more than 3 hours, preferably no more than 2 hours. Preferably, the two-step calcining process is carried out in an inert atmosphere, for example, under a constant flow of an inert gas (e.g. argon, helium, nitrogen, etc.).

The examples below are intended to further illustrate protocols for the method of dehydrogenating the butane-containing hydrocarbon stream and the method of producing the bimetallic catalyst, and are not intended to limit the scope of the claims.

Example 1

Catalyst Preparation:

Bi—Ni oxide based catalysts were prepared using co-impregnation technique, using $Ni(NO_3)_2 \cdot 6H_2O$ (99%, Fisher-Scientific) and $Bi(NO_3)_3 \cdot 5H_2O$ (98%, Fluka-Garantie) as precursors for metals. In a typical preparation of supported 30 wt % Bi-20 wt % Ni catalyst, to a solution of 0.99 g of nickel nitrate hexahydrate in 160 ml of distilled water, 1.392 g of bismuth nitrate pentahydrate and 2.0 g of solid support were added and the mixture stirred at 55° C. about 2 h. The resulting suspension was left overnight for impregnation. After drying the suspension for 3 h at 120° C., the resulting powder was pressed into pellets form, crushed to break up the crumbs and then sieved into 500-850 mesh granules.

Example 2

Conversion of Butane to Alkenes

The catalytic oxidative conversion of n-butane was carried out in an automated fixed bed fixed bed reactor with continuous flow system purchased from Microtrac Bel Company, Japan. The reactor comprises quartz tubular reactor, placed inside stainless steel furnace which passes through the reactor furnace thermo well wall. Typically 300 mg of the as-synthesized catalyst was placed into the quartz reaction tube (length of heating zone=18 cm, inner diameter=8 mm). Prior to the reaction, the catalyst was pretreated at high temperature under flowing nitrogen. After which the catalyst was cooled down to the reaction temperature using nitrogen. The reactions were carried out at temperature in the range of 350-550° C. with reactant feed ratio of $O_2$/n-butane in the range of 1.0 mole/mole to 6 mole/mole.

Taking into account the exothermic nature of oxy-dehydrogenation reaction, the catalyst bed temperature was monitored by a thermocouple, which inserted into thermocouple well. The products and reactants were analyzed by an Agilent 7890N gas chromatograph equipped with flame ionization detector (FID) and GC-Gas Pro capillary column (L: 60 m and ID: 0.032 mm) analyzing the hydrocarbons and oxygenates. The thermal conductivity detector (TCD), Shin Carbon 80/100 mesh SS Column (Helium as a carrier gas) and MSSA 60/80 mesh SS Column (Argon as a carrier gas) were also attached with the GC system for detection of gases including CO, $CO_2$, $O_2$, $N_2$ and $H_2$. The effluents were identified by comparing with authentic samples. The conversion of n-butane and selectivity of products were determined on the basis of carbon balance.

Example 3

The catalytic oxidative conversion of n-butane using unsupported metal oxides of Ni and Bi (Ni—Bi—O) catalyst was studied at $O_2$/n-$C_4H_{10}$ ratios of 2.0 and 4.0 mole/mole, and temperatures of 400 and 500° C. The product distribution is presented in Table 1. The catalytic conversion of n-butane by Ni—Bi—O catalyst was 13.1% at 500° C. The selectivity of ethylene and propylene from the oxidative cracking were 30 and 11.6%, respectively. The unsupported catalyst showed high selectivity towards dehydrogenation (butenes) and partial oxidation (CO) products. The selectivity of butenes and CO decreased with increase in temperature. The result indicates that a suitable catalyst support is needed to disperse the active metal oxides for effective performance.

TABLE 1 n-Butane conversion & product selectivity over unsupported Ni—Bi—O catalyst

| Catalyst | Ni—Bi—O | Ni—Bi—O |
|---|---|---|
| Temperature | 400° C. | 500° C. |
| $^a$$O_2$/n$C_4H_{10}$ | 4.0 | 2.0 |
| n$C_4H_{10}$ conversion | 1.3 | 13.1 |
| $^b$Selectivity | mole % | mole % |
| CO | 22.3 | 1.8 |
| $CO_2$ | 9.5 | 33.8 |
| $C_1$ | 0.0 | 0.0 |
| $C_2$ | 0.0 | 0.0 |
| $C_2^=$ | 6.9 | 30.0 |
| $C_3$ | 0.0 | 0.0 |
| $C_3^=$ | 7.7 | 11.6 |
| t-2-$C_4^=$ | 11.5 | 3.7 |
| 1-$C_4^=$ | 31.4 | 12.3 |
| c-2-$C_4^=$ | 10.7 | 3.1 |
| BD | 0.0 | 3.6 |
| Sum | 100.0 | 100.0 |
| $C_2^=$ yield | 0.09 | 3.9 |
| $C_3^=$ yield | 0.10 | 1.5 |

$^a$mole/mole,
$^a$abbreviation: $C_1$ methane, $C_2$ ethane, $C_2^=$ ethylene, $C_3$ propane, $C_3^=$ propene, t-2-$C_4^=$ trans-2-butene, 1-$C_4^=$ 1-butene, c-2-$C_4^=$ cis-2-butene, and BD butadiene.

Example 4

Active metal oxides of Ni and Bi were supported on a calcined zirconium oxide. The calcination was carried out at a temperature of 550° C. for 3 h. Products distribution of n-butane conversion over Ni—Bi/$ZrO_2$ catalyst is presented in Table 2. The supported catalyst showed higher conversion compared with the unsupported Ni—Bi—O catalyst. Ethylene yield increased from 3.9 C % with unsupported Ni—Bi—O to 6.4 C % with supported catalyst. The Ni—Bi/ZrO$_2$ catalyst showed enhanced dehydrogenation product selectivity especially butadiene (2nd dehydrogenation product) as it increased from 3.6% with Ni—Bi—O catalyst to 29.2% with Ni—Bi/ZrO$_2$ at reaction temperature of 500° C. The catalyst showed low selectivity towards partial oxidation products. Lower olefins yields increased at lower reaction temperature of 400° C. Ethylene yield increased from 6.4 C % to 9.5 C % when the reaction temperature was reduced from 500° C. to 400° C.

TABLE 2 n-Butane conversion & product selectivity over calcined Ni—Bi—O/Zirconia

|  | Ni—Bi—O/Zirconia support catalyst | |
| --- | --- | --- |
| Temperature | 400° C. | 500° C. |
| $^a$O$_2$/nC$_4$H$_{10}$ | 4.0 | 2.0 |
| nC$_4$H$_{10}$ conversion | 41.4 | 29.4 |
| $^b$Selectivity | | |
| CO | 0.2 | 0.2 |
| CO$_2$ | 24.4 | 23.6 |
| C$_1$ | 0.7 | 3.2 |
| C$_2$ | 0.0 | 0.2 |
| C$_2^=$ | 22.9 | 21.9 |
| C$_3$ | 0.0 | 0.2 |
| C$_3^=$ | 3.8 | 5.0 |
| t-2-C$_4^=$ | 6.6 | 5.2 |
| 1-C$_4^=$ | 19.1 | 7.7 |
| c-2-C$_4^=$ | 5.8 | 3.8 |
| BD | 16.8 | 29.2 |
| Sum | 100.0 | 100.0 |
| C$_2^=$ yield | 9.5 | 6.4 |
| C$_3^=$ yield | 1.6 | 1.5 |

$^a$mole/mole,
$^b$abbreviation: C$_1$ methane, C$_2$ ethane, C$_2^=$ ethylene, C$_3$ propane, C$_3^=$ propene, t-2-C$_4^=$ trans-2-butene, 1-C$_4^=$ 1-butene, c-2-C$_4^=$ cis-2-butene, and BD butadiene.

Example 5

Active metal oxides of Ni and Bi were deposited on an uncalcined zirconium oxide (zirconium hydroxide) support. Products distribution of n-butane conversion over the catalyst is presented in Table 3. The un-calcined zirconium oxide support showed improved the dispersion of the catalyst leading to increase in the active lattice oxygen species selective towards cracking products (propylene and ethylene). Compared with the calcined zirconia supported catalyst, the catalyst showed a high increase in the yields of both ethylene and propylene from 6.4 C % and 1.5 C % to 10.1 C % and 2.5 C %, respectively at reaction temperature of 500° C. The un-calcined zirconium oxide supported catalyst showed a decreased in dehydrogenation product yields. Also, the catalyst showed no selectivity toward partial oxidation products (CO). A substantial increase in the yield of 15.7% ethylene and 2.6% propylene was observed at a low reaction temperature of 400° C. with the instant catalyst compare to that of the catalyst of example 4.

TABLE 3 n-Butane conversion & selectivities over Ni—Bi—O/Zirconia support at reactions temperature of 400 and 500° C.

| Zirconia support species | ZrO$_2$ sol | ZrO$_2$ sol |
| --- | --- | --- |
| Temperature | 400 | 500 |
| O$_2$/nC$_4$H$_{10}$ | 4.0 | 2.0 |
| nC$_4$H$_{10}$ conversion | 40.5 | 28.2 |

TABLE 3-continued n-Butane conversion & selectivities over Ni—Bi—O/Zirconia support at reactions temperature of 400 and 500° C.

| Selectivity | | |
| --- | --- | --- |
| CO | 0.0 | 0.0 |
| CO$_2$ | 40.9 | 38.6 |
| C$_1$ | 0.9 | 2.3 |
| C$_2$ | 0.3 | 0.6 |
| C$_2^=$ | 38.8 | 35.7 |
| C$_3$ | 0.0 | 0.4 |
| C$_3^=$ | 6.3 | 8.8 |
| t-2-C$_4^=$ | 1.9 | 1.7 |
| 1-C$_4^=$ | 6.8 | 3.5 |
| c-2-C$_4^=$ | 1.4 | 1.1 |
| BD | 2.8 | 7.3 |
| Sum | 100.0 | 100.0 |
| C$_2^=$ yield | 15.7 | 10.1 |
| C$_3^=$ yield | 2.6 | 2.5 |

$^a$mole/mole,
$^b$abbreviation: C$_1$ methane, C$_2$ ethane, C$_2^=$ ethylene, C$_3$ propane, C$_3^=$ propene, t-2-C$_4^=$ trans-2-butene, 1-C$_4^=$ 1-butene, c-2-C$_4^=$ cis-2-butene, and BD butadiene.

Example 6

The catalyst used in this example comprises of the active metal oxides of Ni and Bi deposited on low-aluminum zeolite, Silicalite-I or Ge-MFI silicate. The product distribution is presented in Table 4. The low-aluminum zeolite showed dispersion ability and increased the active lattice oxygen species selective towards cracking products (propylene and ethylene). The low-aluminum supported catalyst gave 4.7 C % and 1.9 C % as the yields of ethylene and propylene, respectively at reaction temperature of 500° C. The low-aluminum zeolite supported catalyst showed a decreased in dehydrogenation product yields. These catalysts also showed low selectivity toward partial oxidation products. Light olefins yields of 6.2 C % for ethylene and 2.7 C % for propylene were obtained at a reaction temperature of 500° C. with the Ge-MFI silicate supported catalyst.

TABLE 4 n-Butane conversion & product selectivities over Ni—Bi—O/Zeolite support at reaction temperature 500° C.$^a$

| Zeolite support species | Low-aluminum MFI zeolite | Silicalite-I | Ge-silicate MFI zeolite |
| --- | --- | --- | --- |
| nC$_4$H$_{10}$ conversion | 16.1 | 16.9 | 37.0 |
| Selectivity | | | |
| CO | 9.0 | 5.8 | 5.3 |
| CO$_2$ | 32.9 | 12.6 | 19.2 |
| C$_1$ | 5.3 | 0.0 | 4.1 |
| C$_2$ | 0.7 | 0.0 | 0.0 |
| C$_2^=$ | 29.0 | 10.1 | 16.7 |
| C$_3$ | 0.0 | 0.7 | 0.3 |
| C$_3^=$ | 11.7 | 7.6 | 7.4 |
| t-2-C$_4^=$ | 4.4 | 10.9 | 8.2 |
| 1-C$_4^=$ | 2.9 | 26.4 | 19.1 |
| c-2-C$_4^=$ | 3.3 | 9.6 | 5.9 |
| BD | 0.8 | 16.3 | 13.8 |
| Sum | 100.0 | 100.0 | 100.0 |
| C$_2^=$ yield | 4.7 | 1.7 | 6.2 |
| C$_3^=$ yield | 1.9 | 1.3 | 2.7 |

$^a$O$_2$/n-butane = 2.0 mol/mol,
$^b$abbreviation: C$_1$ methane, C$_2$ ethane, C$_2^=$ ethylene, C$_3$ propane, C$_3^=$ propene, t-2-C$_4^=$ trans-2-butene, 1-C$_4^=$ 1-butene, c-2-C$_4^=$ cis-2-butene, and BD butadiene.

Example 7

Active metal oxides of Ni and Bi were modified with Fe, Co, Mo and/or W. The product distribution is presented in Table 5. The Fe/Co, Mo and/or W modified Ni—Bi oxide catalysts showed improved dispersion ability and increased the active lattice oxygen species selective towards cracking products, i.e., propylene and ethylene. The Ni—Bi—W catalyst showed 3.7 C % and 1.1 C % as the yields of ethylene and propylene, respectively at 500° C. The modified metal oxide catalysts showed an increased in dehydrogenation and partial oxidation product yields. Light olefins yields of 10.7 C % for ethylene and 0.4 C % for propylene were obtained at a reaction temperature of 500° C. with the Ni—Fe—Co—Bi catalysts.

TABLE 5 n-Butane conversion & product selectivities over modified Ni—Bi—O/alumina at reaction temperature 500° C.[a]

| Metal oxide system | Ni—Fe—Co—Bi | Ni—Bi—Mo | Ni—Bi—W |
|---|---|---|---|
| $nC_4H_{10}$ conversion | 39.6 | 28.3 | 30.1 |
| Selectivity | | | |
| CO | 0.3 | 17.2 | 20.4 |
| $CO_2$ | 27.6 | 10.9 | 13.5 |
| $C_1$ | 1.5 | 2.4 | 4.3 |
| $C_2$ | 0.0 | 0.0 | 0.0 |
| $C_2^=$ | 27.3 | 10.2 | 12.2 |
| $C_3$ | 0.0 | 0.4 | 0.0 |
| $C_3^=$ | 1.0 | 2.0 | 3.7 |
| $t\text{-}2\text{-}C_4^=$ | 4.9 | 6.1 | 4.1 |
| $1\text{-}C_4^=$ | 6.4 | 5.9 | 3.1 |
| $c\text{-}2\text{-}C_4^=$ | 3.8 | 4.8 | 3.1 |
| BD | 27.3 | 40.1 | 35.7 |
| Sum | 100.0 | 100.0 | 100.0 |
| $C_2^=$ yield | 10.7 | 2.9 | 3.7 |
| $C_3^=$ yield | 0.4 | 0.6 | 1.1 |

[a]$O_2$/n-butane = 2.0 mol/mol,
[b]abbreviation: $C_1$ methane, $C_2$ ethane, $C_2^=$ ethylene, $C_3$ propane, $C_3^=$ propene, $t\text{-}2\text{-}C_4^=$ trans-2-butene, $1\text{-}C_4^=$ 1-butene, $c\text{-}2\text{-}C_4^=$ cis-2-butene, and BD butadiene.

Example 8

The active metal oxides of Ni and Bi were modified with Ga and deposited on mesoporous silica foam (MSF). Products distribution of n-butane conversion over Ni—Bi/MSF catalyst is presented in Table 6. The Ga modified catalyst showed enhanced dispersion ability and increased the active lattice oxygen species selective towards cracking products, i.e., propylene and ethylene. Compared with the unmodified catalyst, this catalyst showed doubled the yields of both ethylene and propylene from 3.2 and 0.6 to 6.0 and 1.2 respectively at reaction temperature of 500° C. The Ga modified catalyst showed a decreased in dehydrogenation product yields. Also, Ga-modified catalyst showed high selectivity toward partial oxidation products (syngas).

TABLE 6 n-Butane conversion & selectivities over Ni—Bi—O/ Silica foam support at reactions temperature 500° C.[a]

| Metal species | Ni—Bi | Ni—Ga—Bi |
|---|---|---|
| Temp-$O_2$/$nC_4H_{10}$ | 500-2 | 500-2 |
| $nC_4H_{10}$ conversion | 40.5 | 28.2 |
| Selectivity | | |
| CO | 1.6 | 22.6 |
| $CO_2$ | 32.3 | 23.9 |
| $C_1$ | 0.2 | 2.5 |
| $C_2$ | 0.0 | 0.2 |
| $C_2^=$ | 8.6 | 15.3 |
| $C_3$ | 0.3 | 0.1 |
| $C_3^=$ | 1.7 | 3.0 |
| $t\text{-}2\text{-}C_4^=$ | 5.8 | 4.2 |
| $1\text{-}C_4^=$ | 6.9 | 4.2 |
| $c\text{-}2\text{-}C_4^=$ | 4.1 | 3.1 |
| BD | 38.5 | 20.9 |
| Sum | 100.0 | 100.0 |
| $C_2^=$ yield | 3.2 | 6.0 |
| $C_3^=$ yield | 0.6 | 1.2 |

[a]$O_2$/n-butane = 2.0 mol/mol,
[b]abbreviation: $C_1$ methane, $C_2$ ethane, $C_2^=$ ethylene, $C_3$ propane, $C_3^=$ propene, $t\text{-}2\text{-}C_4^=$ trans-2-butene, $1\text{-}C_4^=$ 1-butene, $c\text{-}2\text{-}C_4^=$ cis-2-butene, and BD butadiene.

One objective of the present invention is to provide a catalytic oxidative process for direct conversion of n-butane to light olefins, mainly ethylene and propylene. The catalyst used in the oxidative cracking reaction includes one ore more metal oxides of Ni and Bi supported on zirconium oxide, low aluminum zeolite and/or mesoporous silica foam to enhance the production of light olefins. Generally, the method of the invention involves co-feeding a stream of hydrocarbon containing butanes, air as a source of oxygen and inert gas into a fixed bed reactor. The oxidative cracking of feedstock hydrocarbon resulted in production of ethylene and propylene at lower temperature compared to steam or catalytic cracking without oxygen. The degraded catalyst can be regenerated in-situ by an oxidizing atmosphere.

The invention claimed is:

1. A method of dehydrogenating a butane-containing hydrocarbon stream, comprising:
    contacting a mixture of the butane-containing hydrocarbon stream and oxygen with a bimetallic catalyst supported on a solid support of low aluminum MFI zeolite to form a product stream comprising one or more oxygenated products, ethylene, and propylene,
    wherein the bimetallic catalyst consists of nickel oxide and bismuth oxide,
    wherein the bimetallic catalyst has an average particle size in a range of 0.1 to 2 mm,
    wherein the low aluminum MFI zeolite comprises aluminum and has a silicon to aluminum atomic ratio of at least 250, and
    wherein the solid support of low aluminum MFI zeolite is modified with Fe, Co, Ga, Mo and/or W.

2. The method of claim 1, further comprising separating the ethylene and the propylene from the oxygenated products.

3. The method of claim 1, wherein the butane-containing hydrocarbon stream comprises butane, isobutene, raffinate-I, raffinate-II, rafinate-III, rafinate-IV, or a combination thereof.

4. The method of claim 1, wherein the butane is n-butane.

5. The method of claim 3, wherein the nickel oxide and bismuth oxide is prepared by impregnating un-calcined solid support.

6. The method of claim 1, wherein a weight percent of nickel in the bimetallic catalyst is within a range of 15 wt % to 25 wt %, and wherein a weight percent of bismuth in the bimetallic catalyst is within a range of 25 wt % to 35 wt %, each relative to the total weight of the bimetallic catalyst.

7. The method of claim 1, wherein the bimetallic catalyst supported on the solid support is subjected to calcination at 250-400° C. for at least 0.5 hours and at 560-640° C. for at least 1 hour prior to the contacting.

8. The method of claim 1, wherein the butane-containing hydrocarbon stream is contacted with the bimetallic catalyst supported on the solid support at a temperature of 400 to 600° C., and
wherein a molar ratio of oxygen to butane in the mixture is in a range of 1:1 to 6:1.

9. The method of claim 1, further comprising:
treating the bimetallic catalyst supported on the solid support with an inert gas having a temperature in a range of 300 to 600° C. prior to the contacting.

10. The method of claim 1, wherein the butane-containing hydrocarbon stream is at a pressure in a range of 1-10 bars during the contacting.

11. The method of claim 1, wherein the product stream comprises the ethylene and propylene in a molar ratio of (moles of ethylene and moles of propylene):(all other compounds in the product stream) at least 0.6.

12. The method of claim 1, wherein a conversion of butane to ethylene and propylene is in a range of 5 to 30 mol %, and
wherein a combined yield of ethylene and propene is in a range of 3 to 25 mol % based on the conversion of butane.

13. A method of dehydrogenating a butane-containing hydrocarbon stream, comprising:
contacting a mixture of the butane-containing hydrocarbon stream and oxygen at a pressure in a range of 1-10 bars with a bimetallic catalyst supported on a solid support of low aluminum MFI zeolite to form a product stream comprising ethylene and propylene,
wherein the butane-containing hydrocarbon stream is contacted with the bimetallic catalyst at a temperature of 450 to 550° C.,
wherein the bimetallic catalyst consists of nickel oxide and bismuth oxide,
wherein the bimetallic catalyst has an average particle size in a range of 0.1 to 2 mm,
wherein the low aluminum MFI zeolite comprises aluminum and has a silicon to aluminum atomic ratio of at least 250, and
wherein the solid support of low aluminum MFI zeolite is modified with Fe, Co, Ga, Mo and/or W.

14. The method of claim 1, wherein the solid support comprises strontium, and
wherein the solid support has a strontium to aluminum atomic ratio in a range of 2-8.

15. The method of claim 1, wherein the solid support is modified with Ga.

16. The method of claim 1, wherein the solid support is modified with W.

17. The method of claim 1, wherein the solid support is modified with Fe and Co.

18. The method of claim 17, wherein the solid support further comprises strontium, and
wherein the solid support has a strontium to aluminum atomic ratio in a range of 2-8.

19. The method of claim 18, wherein the low aluminum MFI zeolite has a silicon to aluminum atomic ratio of 250 to 300,
wherein a weight percent of nickel in the bimetallic catalyst is within a range of 19 wt % to 21 wt %, and
wherein a weight percent of bismuth in the bimetallic catalyst is within a range of 29 wt % to 31 wt %, each relative to the total weight of the bimetallic catalyst.

* * * * *